(12) United States Patent
Takahashi et al.

(10) Patent No.: US 10,092,460 B2
(45) Date of Patent: Oct. 9, 2018

(54) ABSORBENT ARTICLE

(71) Applicant: LIVEDO CORPORATION, Ehime (JP)

(72) Inventors: Yuki Takahashi, Tokushima (JP); Masatoshi Ikeuchi, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 378 days.

(21) Appl. No.: 14/777,701

(22) PCT Filed: Oct. 21, 2013

(86) PCT No.: PCT/JP2013/078453
§ 371 (c)(1),
(2) Date: Sep. 16, 2015

(87) PCT Pub. No.: WO2014/147879
PCT Pub. Date: Sep. 25, 2014

(65) Prior Publication Data
US 2016/0278996 A1    Sep. 29, 2016

(30) Foreign Application Priority Data
Mar. 18, 2013   (JP) .................................. 2013-055621

(51) Int. Cl.
*A61F 13/15*      (2006.01)
*A61F 13/494*     (2006.01)
(Continued)

(52) U.S. Cl.
CPC .... *A61F 13/4942* (2013.01); *A61F 13/15268* (2013.01); *A61F 13/493* (2013.01);
(Continued)

(58) Field of Classification Search
CPC ................ A61F 13/4942; A61F 13/493; A61F 13/49433; A61F 13/15268; A61F 13/49003; A61F 13/49413; A61F 13/505
(Continued)

(56) References Cited

U.S. PATENT DOCUMENTS 5,582,606 A    12/1996  Bruemmer et al.
6,440,117 B1    8/2002  Itoh et al.
(Continued)

FOREIGN PATENT DOCUMENTS

JP    52-42916    10/1977
JP    6-209967    8/1994
(Continued)

OTHER PUBLICATIONS

International Search Report dated Jan. 21, 2014 in International Application No. PCT/JP2013/078453.
(Continued)

*Primary Examiner* — Jacqueline Stephens
(74) *Attorney, Agent, or Firm* — Wenderoth, Lind & Ponack, L.L.P.

(57) ABSTRACT

An absorbent article comprising a top sheet, a back sheet and an absorbent core provided therebetween; wherein flap sheets having a center region, end regions and intermediate regions positioned therebetween are provided on both sides of the top sheet in a width direction, the flap sheet has a base part facing to the top sheet and a rising part extending from the base part and formed by folding the flap sheet at an inner edge of the base part in the width direction, the center region and the end region of the base part are joined to the top sheet and/or the back sheet at an inner position, in the width direction, of that the intermediate region of the base part is joined to the top sheet and/or the back sheet, and the rising part is joined to the base part at the end region.

10 Claims, 6 Drawing Sheets

(51) Int. Cl.
*A61F 13/505* (2006.01)
*A61F 13/493* (2006.01)

(52) U.S. Cl.
CPC ....... *A61F 13/49413* (2013.01); *A61F 13/505* (2013.01); *A61F 2013/4948* (2013.01)

(58) Field of Classification Search
USPC ............... 604/385.24, 385.28, 385.25, 385.3
See application file for complete search history.

(56) References Cited

U.S. PATENT DOCUMENTS

| | | |
|---|---|---|
| 2002/0123733 A1 | 9/2002 | Itoh et al. |
| 2004/0122410 A1 | 6/2004 | Itoh et al. |
| 2013/0172841 A1 | 7/2013 | Ichikawa et al. |

FOREIGN PATENT DOCUMENTS

| | | |
|---|---|---|
| JP | 11-285510 | 10/1999 |
| JP | 2000-288012 | 10/2000 |
| JP | 2000-354607 | 12/2000 |
| JP | 2010-94334 | 4/2010 |
| JP | 2012-75648 | 4/2012 |
| JP | 2012-217652 | 11/2012 |

OTHER PUBLICATIONS

Japanese Office Action dated Apr. 4, 2017 in corresponding Japanese patent application No. 2013-055621 (with English translation).
Taiwanese Office Action dated Apr. 19, 2017 in corresponding Taiwanese patent application No. 102139021 (with English translation).

ABSORBENT ARTICLE

TECHNICAL FIELD

The present invention relates to an absorbent article such as a disposable diaper, an incontinence pad (including a light incontinence pad) and a sanitary napkin.

BACKGROUND ART

In an absorbent article, leakproof walls (leakproof cuffs) are often provided on both lateral sides of a skin-facing side thereof to prevent lateral leaking of urine and the like excreted from a wearer. Various absorbent articles provided with leakproof walls have been proposed in the past, and for example, Patent Literature 1 discloses an absorbent article provided with leakproof walls, which is folded in two at a fold line at an inner position in the width direction, and Patent Literature 2 discloses an absorbent article to which leakproof walls are joined to be fixed, wherein a center part, with respect to the front-rear direction, of the leakproof wall is accordion-folded so that height of the leakproofwall is lowered at the center part.

CITATION LIST

Patent Literature

Patent Literature 1
  Japanese Unexamined Laid-open Patent Application Publication No. H11-285510
Patent Literature 2
  Japanese Unexamined Laid-open Patent Application Publication No. 2000-354607

SUMMARY OF INVENTION

Technical Problem

As explained above, leakproof walls in variety of shapes have been proposed in the past, and it is desired that urine and the like can be lead properly to a space between the leakproof walls provided on both sides in the width direction and the urine and the like which the absorbent article has been received does not leak laterally, as a fundamental property of the leakproof wall installed in the absorbent article. The present invention has been achieved in view of the above circumstances, and the object of the present invention is to provide an absorbent article provided with a leakproof wall that is able to receive urine and the like excreted from a wearer properly and is less likely to occur lateral leakage of urine and the like.

Solution to Problem

An absorbent article of the present invention which solves the above problems comprises a top sheet, a back sheet and an absorbent core provided therebetween, and has a front-rear direction and a width direction; wherein flap sheets having a center region, end regions and intermediate regions positioned therebetween are provided on both sides of the top sheet in the width direction; the flap sheet has a base part facing to the top sheet and a rising part extending from the base part and formed by folding the flap sheet at an inner edge of the base part in the width direction; the center region and the end region of the base part are joined to the top sheet and/or the back sheet at an inner position, in the width direction, of that the intermediate region of the base part is joined to the top sheet and/or the back sheet; and the rising part is joined to the base part at the end region.

Since the absorbent article of the present invention is provided with the flap sheet which is formed in the above manner, the rising part is likely to stand outward in the width direction, whereby the absorbent article easily receives urine and the like excreted from a wearer, properly. Further, even when the wearer sits, the flap sheet easily stands outward in the width direction stably at the center region. Meanwhile, the intermediate region of the flap sheet is less likely to be pressed when the wearer sits; and therefore, a leakproof wall formed by the flap sheet is formed high, whereby lateral leakage of urine and the like is easily prevented.

It is preferred that the rising part is provided with a flap elastic member extending in the front-rear direction and the base part is not provided with an elastic member. When the flap elastic member is provided in this manner, the leakproof wall standing outward in the width direction is easily formed properly by the rising part rising.

In the rising pan, a plurality of the flap elastic members are preferably disposed so as to be arranged in the width direction. When the flap elastic members are provided in this manner, the rising part is likely to rise in a planar state, thereby contacting wearer's skin so as to encompass buttocks of a wearer.

It is preferred that at least one elastic member is disposed in an area within 5 mm from an outer edge of the rising part in the width direction, as the flap elastic member, and at least one elastic member is disposed in an area within 5 mm from an inner edge of the rising part in the width direction, as the flap elastic member. When the flap elastic member is provided in this manner, the rising part easily rises in a planar state in the entire width direction thereof.

The flap elastic members are preferably disposed in the rising part such that contraction force in an outer side, with respect to the width direction, of the rising part is larger than that in an inner side, with respect to the width direction, of the rising part. When the flap elastic member is provided in this manner, the rising part easily rises in a planar state so as to encompass buttocks of a wearer while an outer edge of the rising part rises higher.

It is preferred that the flap elastic member is attached to the rising part with an adhesive and disposed so as to extend from the center region to the front and rear intermediate regions, wherein an amount of the adhesive applied to a front end part of the flap elastic member is larger than that applied to a rear end part of the flap elastic member. When the flap elastic member is provided in this manner, the rising part tends to be formed such that contractive force in the rear intermediate region is smaller than that in the front intermediate region. Hence, the rising part is less likely to contact hard to wearer's skin at the buttocks, thereby improving wearing feeling. Meanwhile, since the front intermediate region of the rising part is formed to exert larger contractive force, the rising part is likely to contact to wearer's skin closely at a groin of the wearer to prevent lateral leakage from the groin.

The center region and the end region of the base part are preferably joined to the top sheet and/or the back sheet at a 10 mm or more inner position, in the width direction, of that the intermediate region of the base part is joined to the top sheet and/or the back sheet. When the base part is joined to the top sheet and/or the back sheet in this manner, urine and the like can be absorbed over a wide area in the intermediate region by the absorbent article and the higher leakproof can be formed in the intermediate region.

The center region of the base part is preferably joined to the top sheet at an area within 10 mm from the inner edge of the base part in the width direction. When the center region of the base part is joined to the top sheet in this manner, the rising part rises to easily form the leakproof wall standing outward in the width direction.

Advantageous Effects of Invention

According to the absorbent article of the present invention, since a leakproof wall standing outward in the width direction is formed at a crotch of a wearer, urine and the like excreted from the wearer can be received properly. In addition, the leakproof wall is formed high at the intermediate region, that is less likely to be pressed when the wearer sits; and therefore, lateral leakage of urine and the like is prevented properly.

DESCRIPTION OF THE PREFERRED EMBODIMENTS

Figure 1:
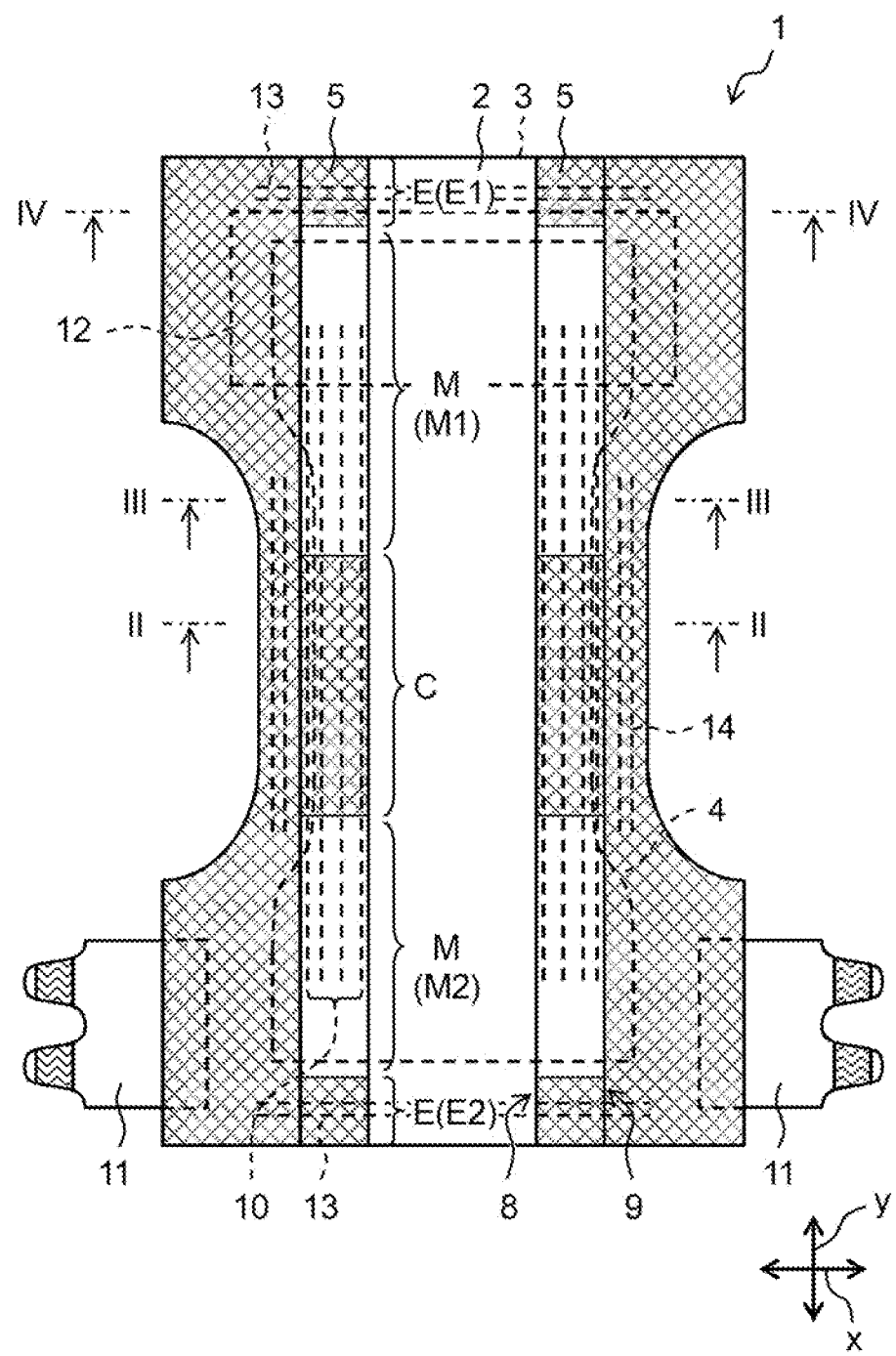
FIG. 1 shows a plan view of a skin-facing side of an open-type disposable diaper as an absorbent article.

An absorbent article of the present invention comprise a top sheet, a back sheet and an absorbent core provided therebetween, and has a front-rear direction and a width direction. Examples of the absorbent article of the present invention include a disposable diaper, an incontinence pad (including a light incontinence pad) and a sanitary napkin are shown.

In the present invention, the front-rear direction of the absorbent article means a direction extending in a front-rear direction at a crotch of a wearer when the wearer wears the absorbent article. The width direction of the absorbent article means a direction orthogonal to the front-rear direction on the same plane as the absorbent article. In addition, a skin-facing side of the absorbent article means a side facing to wearer's skin in wearing the absorbent article and an exterior side of the absorbent article means a side facing opposite to the wearer in wearing the absorbent article.

A shape of the absorbent article is not particularly limited. In the case that the absorbent article is an incontinence pad, examples of the shape of the absorbent article include a substantially rectangular shape, an hourglass shape, a center nipped-in gourd shape, and others.

In the case that the absorbent article is a disposable diaper, the absorbent article has, for example, a front part, a rear part, and a crotch part positioned therebetween and provided with an absorbent core. The disposable diaper may comprise, for example, an exterior member having a front part, a rear part and a crotch part positioned therebetween and an absorbent body comprising a top sheet, a back sheet and an absorbent core provided therebetween, wherein the absorbent body is provided on a skin-facing side of the exterior member. In this case, the shape of the absorbent body may be a substantially rectangular shape and so on. The disposable diaper may be formed such that a laminate comprising a top sheet, a back sheet and an absorbent core provided therebetween has a front part, a rear part and a crotch part positioned therebetween. Here, the front part means a part applied to an abdomen side of a wearer, the rear part means a part applied to a back side of the wearer, and the crotch part means a part positioned between the front part and the rear part and applied to a crotch of the wearer, in wearing the disposable diaper.

In the case that the absorbent article is a disposable diaper, the disposable diaper may be an open-type (tape-type) disposable diaper that is provided with a pair of fastening members on left and right ends of the rear part and is formed into a pants shape by using the fastening members in wearing, or the disposable diaper may be a pants-type disposable diaper that has a waist opening and a pair of leg openings.

The top sheet is a sheet which is located on a wearer's side in wearing the absorbent article and preferably liquid-permeable. As the top sheet, a nonwoven fabric formed from hydrophilic fibers such as cellulose, rayon and cotton; and a nonwoven fabric which is formed from hydrophobic fibers such as polyolefin (e.g., polypropylene, polyethylene), polyester (e.g., PET) and polyamide (e.g., nylon), and in which the hydrophobic fibers are hydrophilized with a surfactant on the surface thereof; can be used, for example. As the top sheet, a woven fabric, a knitted fabric, a plastic film having pores may be also used.

The back sheet is a sheet which is located on an opposite side of a wearer, that is an exterior side, in wearing the absorbent article and preferably liquid-impermeable. As the back sheet, a nonwoven fabric formed from hydrophobic fibers such as polyolefin (e.g., polypropylene, polyethylene), polyester (e.g., PET) and polyamide (e.g., nylon), and a plastic film, can be used, for example. As the back sheet, a laminate of a nonwoven fabric and a plastic film may be also used. In the present invention, the meaning of "liquid-impermeable" includes water-repellent.

The exterior member may be liquid-permeable or liquid-impermeable, and a sheet material usable for the top sheet or the back sheet can be used. The exterior member is preferably formed by laminating an outer sheet on an inner sheet, and more preferably laminating a liquid-impermeable outer sheet on a liquid-permeable inner sheet.

In the case of using a nonwoven fabric as the each above sheet material, a spunbonded nonwoven fabric, an air-through nonwoven fabric, a point-bonded nonwoven fabric, a meltblown nonwoven fabric, an airlaid nonwoven fabric, an SMS nonwoven fabric or the like is preferably used as the nonwoven fabric.

The absorbent core is not particularly restricted as long as it contains an absorbent material which is able to absorb excrement such as urine and the like. As the absorbent core, a clump of an absorbent material, which is formed into a predefined shape, may be used. The absorbent core may be wrapped with a sheet member such as a paper (e.g., a tissue paper and a thin paper) and a liquid-permeable nonwoven fabric. Examples of the absorbent material contained in the absorbent core include, for example, a hydrophilic fiber such as a cellulose fiber (e.g., a crushed pulp fiber) and an absorbent polymer such as polyacrylic absorbent polymer, polyasparaginic absorbent polymer, cellulosic absorbent polymer, and stark-acrylonitrile absorbent polymer. The absorbent material may include a thermal fusion fiber such as a polyolefin (e.g., polyethylene and polypropylene) fiber, a polyester (e.g., PET) fiber and a polyamide (e.g., nylon) fiber. These thermal fusion fibers may be hydrophilized with a surfactant or the like to increase affinity with a bodiliy fluid such as urine.

The absorbent material preferably includes a hydrophilic fiber in view of increasing absorption rate of urine and the like. In addition, in view of enhancing absorption capacity, the absorbent material preferably includes an absorbent polymer. Therefore, the absorbent core preferably contains both a hydrophilic fiber (especially a pulp fiber) and an absorbent polymer. In this case, the absorbent material is preferably formed by mixing an absorbent polymer with a hydrophilic fiber assembly, or dispersing an absorbent polymer on a hydrophilic fiber assembly, for example.

The absorbent core may be a sheet-shaped absorbent body. Examples of the sheet-shaped absorbent body include an object which is formed to contain an absorbent polymer but not contain a pulp fiber between nonwoven fabrics. The sheet-shaped absorbent body formed in this manner enables high absorption capacity since it contains an absorbent polymer between nonwoven fabrics. In addition, since the sheet-shaped absorbent body does not contain a pulp fiber between nonwoven fabrics, it can be formed thin without being bulky.

For the sheet-shaped absorbent body, an absorbent fiber may be used as the absorbent material. Also in this case, the sheet-shaped absorbent body is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group, as disclosed in Japanese Examined Patent Application Publication No. S52-42916. The carboxyl group contained in the absorbent fiber is preferably forms an alkaline metal salt or an ammonium salt. The absorbent fiber also can be prepared by immersing a hydrophilic fiber in acrylic acid to deposit acrylic acid on the surface of the fiber.

A shape (planar shape) of the absorbent core is not limited. The shape of the absorbent core is determined as appropriate according to application, and examples of the shape of the absorbent core include a substantially rectangular shape, an hourglass shape, a center nipped-in gourd shape, a battledore shape and the like.

In the absorbent article of the present invention, flap sheets are provided on both sides, in the width direction, of the top sheet. The flap sheet forms a leakproof wall for preventing lateral leakage of urine and the like excreted from a wearer. The flap sheet is preferably liquid-impermeable, and a sheet material usable for the back sheet can be used.

The flap sheet is folded so as to have a L-shaped or lied V-shaped cross-section in the width direction. Thus, the flap sheet is folded in the width direction at a fold line located medially in the width direction. The thus formed flap sheet has a base part facing to the top sheet and a rising pan extending from the base part and formed by folding the flap sheet at an inner edge of the base part in the width direction.

In the flap sheet, the base part is basically joined to the top sheet. Nevertheless, in the case where the back sheet is provided so as to extend outward beyond the top sheet in the width direction or the back sheet is folded along an edge of the absorbent core in the width direction onto an upper surface of the top sheet, the base part may be joined to the back sheet. The rising part of the flap sheet forms a leakproof wall, which prevents lateral leakage of urine and the like. Here, only a part of the base part is joined to the top sheet and/or the back sheet, and another part of the base part forms the leakproof wall in cooperation with the rising part. An outer edge, with respect to the width direction, of the rising part gives a free end to form an upper end of the leakproof wall in wearing the absorbent article.

The flap sheet has a center region, end regions and intermediate regions positioned therebetween in the front-rear direction. The end regions are regions including an end of the flap sheet in the front-rear direction, and consist of a front end region and a rear end region. The intermediate regions are regions positioned between the center region and the end regions, and consist of a front intermediate region positioned between the center region and the front end region and a rear intermediate region positioned between the center region and the rear end region. That is, the flap sheet has the front end region, the front intermediate region, the center region, the rear intermediate region and the rear end region in this order from the front side in the front-rear direction.

Lengths (length with respect to the front-rear direction) of the center region, the end region and the intermediate region are not particularly limited. For example, provided that relative positon of the flap sheet in the front-rear direction is defined such that the front end is located at 0% and the rear end is located at 100%, the front end region may be located in the region of 0% to 15%, the center region may be located in the region of 25% to 65%, and the rear end region may be located in the region of 85% to 100%. The relative position explained here is measured in the state where an elastic member in the absorbent article is fully stretched (that is, in the state where the elastic member is removed from the absorbent article or in the state where contractile force of the elastic member is not exerted by shredding the elastic member) if the absorbent article is provided with an elastic member. Regarding the below-described various preferable ranges, values obtained by measuring in the same condition are used.

The center region and the end region of the base part are joined to the top sheet and/or the back sheet at an inner position, in the width direction, of that the intermediate region of the base part is joined to the top sheet and/or the back sheet. And the rising part of the flap sheet is joined to the base part at the end region. As the flap sheet is formed in this manner, the center region and the intermediate region are made to be risable. In the absorbent article of the present invention, the center region and the intermediate region of the flap sheet rise to form a leakproof wall, whereat the rising part is likely to stand outward in the width direction, and as a result, the absorbent article easily receives urine and the like excreted from a wearer, properly. Thus, since the flap sheet is folded in such a manner that the base part is joined to the top sheet and/or the back sheet at a further inner position in the width direction at the center region and the free end of the rising part is located at an outer positon in the width direction, the rising part easily stands outward in the width direction from an inner end of a joining area where the base part is joined to the top sheet and/or the back sheet, and as a result, the rising part is likely to form a bowl-shaped cross-section in the width direction, whereby it becomes easy to receive urine and the like excreted from a wearer properly. In addition, as the rising part stands outward in the width direction, the free end of the rising part (namely, the upper end of the leakproof wall) is less likely to contact hard to wearer's skin but is likely to contact to the skin so as to encompass buttocks of the wearer, thereby enhancing wearing feeling. Meanwhile, in the intermediate region, a non-joining area where the base part is not joined to the top sheet or the back sheet is provided so as to extend outward in the width direction beyond the inner end of the joining area of the center region, where the center region of the base part is joined to the top sheet and/or the back sheet; and therefore, urine and the like is likely to diffuse widely in the width direction in the intermediate region to be absorbed by the absorbent core, thereby enabling rapid absorption of urine and the like.

Further, as the center region of the base part is joined to the top sheet and/or the back sheet at the inner position, in the width direction, of that the intermediate region of the base part is joined to the top sheet and/or the back sheet, the leakproof wall formed by the flap sheet easily stands outward in the width direction stably. Explaining about this in more detail, the center region of the flap sheet is likely to be squashed when the wearer sits, and hence, if the leakproof wall formed by the flap sheet is too high, the leakproof wall becomes less likely to stably stand outward in the width direction. However, according to the absorbent article of the present invention, since the center region of the base part is joined to the top sheet and/or the back sheet at the inner position, in the width direction, of that the intermediate region of the base part is joined to the top sheet and/or the back sheet, the height of the leakproof wall, which is formed by the flap sheet, at the center region is formed lower than that at the intermediate region, and as a result, the leakproof wall could stably stand outward in the width direction. Meanwhile, the intermediate region of the flap sheet is less likely to be pressed when the wearer sits, and hence, the height of the leakproof wall at the intermediate region is formed higher than that at the center region, whereby lateral leakage of urine and the like is easily prevented.

The joining area where the base part is joined to the top sheet and/or the back sheet may be provided continuously or may be provided intermittently. For example, the joining area may be provided so as to extend in the front-rear direction and intermittently in the width direction. In the present invention, the inner end, with respect to the width direction, of the joining area at the center region and the inner end of the joining area at the end region only have to be located at an inner position, in the width direction, of the inner end of the joining area at the intermediate region.

The base part of the flap sheet is preferably formed so as to have a certain width, and for example, length of the base part in the width direction is preferably 15 mm or more, and more preferably 20 mm or more. The rising part of the flap part is also preferably formed so as to have a certain width, and for example, length of the rising part in the width direction is preferably 10 mm or more, and more preferably 15 mm or more. Meanwhile, when the rising part of the flap sheet is formed too wide, the rising part may not to stand properly, and so the length of the rising part in the width direction is preferably 50 mm or less, and more preferably 40 mm or less.

The center region of the base part is preferably joined to the top sheet. When the absorbent article is configured in this manner, the top sheet can be made wider and performance of the absorbent article for absorbing urine and the like can be enhanced. Further, it is preferred that the end region of the base part is also joined the top sheet in view of preventing leakage of urine and the like in the front-rear direction. Meanwhile, the intermediate region of the base part may be joined to the top sheet or may be joined to the back sheet; however, in view of easily-manufacturing of the absorbent article, the intermediate region of the base part is also preferably joined to the top sheet.

It is preferred that the center region of the center region of the base part is joined to the top sheet at an inner position as possible. Therefore, the center region of the base part is preferably joined to the top sheet at an area within 10 mm (more preferably within 8 mm and even more preferably within 5 mm) from the inner edge of the base part in the width direction. When the center region of the base part is joined to the top sheet in this manner, the rising part rises to easily form the leakproof wall standing outward in the width direction. The end region of the base part is also preferably joined to the top sheet at an inner position as possible. Therefore, the end region of the base part is preferably joined to the top sheet at an area within 10 mm (more preferably within 8 mm and even more preferably within 5 mm) from the inner edge of the base part in the width direction.

In the intermediate region of the base part, the non-joining area where the base part is not joined to the top sheet or the back sheet is preferably formed so as to have a certain width. Therefore, it is preferred that the center region and the end region of the base part are joined to the top sheet and/or the back sheet at a 10 mm or more inner position (more preferably at a 15 mm or more inner position and even more preferably at a 20 mm or more inner position), in the width direction, of that the intermediate region of the base part is joined to the top sheet and/or the back sheet. When the non-joining area where the base part is not joined to the top sheet or the back sheet is formed in this manner in the intermediate region, urine and the like can be absorbed over a wide area in the intermediate region by the absorbent article and the higher leakproof wall is able to be formed at the intermediate region. Meanwhile, when the non-joining area where the base part is not joined to the top sheet or the back sheet is excessively formed in the intermediate region, wearing feeling or handleability of the absorbent article is likely to be deteriorated; and hence, regarding the joining area where the base part is joined to the top sheet and/or the back sheet, the inner end of the joining area at the center region and the end region is preferably located at an 80 mm or less inner position, in the width direction, from the inner end of the joining area at the intermediate region.

The flap sheet may be composed of one layer or a plurality of layers. Joining of the base part of the flap sheet to the top sheet and/or the back sheet or joining of the rising part to the base part in the flap sheet may be conducted by a known joining means such as an adhesive, heat-sealing, ultrasonic fusion bonding or the like.

The flap sheet is preferably provided with a flap elastic member. When the flap sheet is provided with a flap elastic member, the flap sheet easily rises by contraction force of the elastic member to form the leakproof wall properly. The flap elastic member may be disposed on either or both surface(s) of the flap sheet or may be disposed between layers constituting the flap sheet.

It is preferred that the flap elastic member is provided at the rising part so as to extend in the front-rear direction. Here, the flap elastic member is preferably fixed to the rising pan in a stretched state in the front-rear direction. When the flap elastic member is provided in this manner, the rising part rises and the leakproof wall standing outward in the width direction is easily formed properly. On the other hand, it is preferred that the base part is not provided with an elastic member. For making the rising part stand outward in the width direction, it is preferred that a lower end of the standing rising part (that is, an inner edge of the rising part) is located at an inner position as possible; however, when the base part is provided with an elastic member, the base part rises to shift an upper end of the base part (that is, the inner edge of the rising part) to an outer positon in the width direction, that makes it difficult for the rising part to stand outward in the width direction.

It is preferred that a plurality of the flap elastic members are disposed in the rising part so as to be arranged in the width direction. When the flap elastic members are provided in this manner, the rising part is likely to rise in a planar state, thereby contacting wearer's skin so as to encompass buttocks of a wearer. Preferably, three or more of the flap elastic members are disposed in the rising part so as to be arranged in the width direction.

In the case that the plurality of the flap elastic members are disposed in the rising part, it is preferred that at least one elastic member is disposed in an area within 5 mm (more preferably within 2 mm and even more preferably within 1 mm) from an outer edge of the rising part in the width direction, as the flap elastic member, and at least one elastic member is disposed in an area within 5 mm (more preferably within 2 mm and even more preferably within 1 mm) from an inner edge of the rising part in the width direction, as the flap elastic member. When the flap elastic member is provided in this manner, the rising part easily rises in a planar state in the entire width direction thereof. More preferably, at least one of another elastic member is further disposed in an area more than 5 mm distance from the inner edge and the outer edge of the rising part in the width direction.

In the case that the plurality of the flap elastic members are disposed in the rising part, the flap elastic members are preferably disposed in the rising part such that contraction force in an outer side, with respect to the width direction, of the rising part is larger than that in an inner side, with respect to the width direction, of the rising part. When the flap elastic member is provided in this manner, the rising part easily rises in a planar state so as to encompass buttocks of a wearer while the outer edge of the rising part rises higher.

For disposing the flap elastic members such that contraction force in the outer side, with respect to the width direction, of the rising part is larger than that in the inner side, with respect to the width direction, of the rising part, elastic members may be fixed to the flap sheet so that contraction force of an elastic member (an outer elastic member) disposed at the outer side, with respect to the width direction, of the rising part is stronger than that of an elastic member (an inner elastic member) disposed at the inner side, with respect to the width direction, of the rising part. Concretely, the outer elastic member may be fixed to the flap sheet at a higher stretching rate than the inner elastic member, or an elastic member having higher modulus of elasticity in tension may be used in the outer elastic member than that in the inner elastic member. In the case where 3 or more of the flap elastic members are disposed, elastic members may be disposed such that interval between the elastic members is shorter in an outer position, with respect to the width direction, in the rising part.

The flap elastic member is preferably disposed so as to extend from the center region to the front and rear intermediate regions, thereby forming the leakproof wall properly by the flap elastic member. Here, it is preferable that the flap elastic member is not disposed at the end region.

It is preferred that the flap elastic member is attached to the rising part by applying an adhesive to the flap elastic member. When the flap elastic member is attached to the rising part in this way, a part of the rising part where the flap elastic member is not disposed comes to be made that an adhesive is not applied to, thereby making the rising part soft to improve its textures. Thus, in this case, the rising part has an adhesive-non-applied area between the flap elastic members, and the rising part is made soft at the adhesive-non-applied area. For example, the flap elastic member is preferably attached to the flap sheet as follows. That is, it is preferred that the flap sheet is composed of a plurality of layers and the flap elastic member is attached to the flap sheet by providing the flap elastic member, which an adhesive has been applied to, between the plurality of layers of the flap sheet.

It is preferred that the flap elastic member is attached to the rising part with an adhesive and disposed so as to extend from the center region to the front and rear intermediate regions, wherein an amount of the adhesive applied to a front end part of the flap elastic member is larger than that applied to a rear end part of the flap elastic member. When the flap elastic member is provided in this manner, tension of the rear end part is relaxed relative to the front end part in the flap elastic member in mounting the stretched flap elastic member to the flap sheet, whereby the rising part tends to be formed such that contractive force in the rear intermediate region is smaller than that in the front intermediate region. Since the rear intermediate region is a part which contacts to buttocks of a wearer, the rising part is less likely to contact hard to the skin at the buttocks of the wearer, thereby improving wearing feeling. Meanwhile, the front intermediate region is a part which contacts to a groin of a wearer, and since a human body is shaped such that an area from a crotch to a groin takes the form of a relatively acute angle, an interspace is likely to be created between the rising part and the wearer's skin in wearing the absorbent article. However, when the front intermediate region of the rising part is formed to exert larger contractive force, the rising part is likely to contact to wearer's skin closely to prevent lateral leakage from the groin.

Elastic materials such as a polyurethane thread, a polyurethane film, a natural rubber, that are generally used for absorbent articles, can be used for the flap elastic member. The flap elastic member is preferably fixed in a stretched state with an adhesive such as a hot-melt adhesive. For example, a polyurethane thread having a fineness of 100 dtex to 2,500 dtex is stretched at a ratio of 1.1 to 5.0 times to be fixed. As the adhesive, a rubber hot-melt adhesive is preferably used.

Next, examples of the absorbent article of the present invention are explained, referring to drawings. However, the present invention is not limited to the embodiments shown in the drawings.

Figure 2:
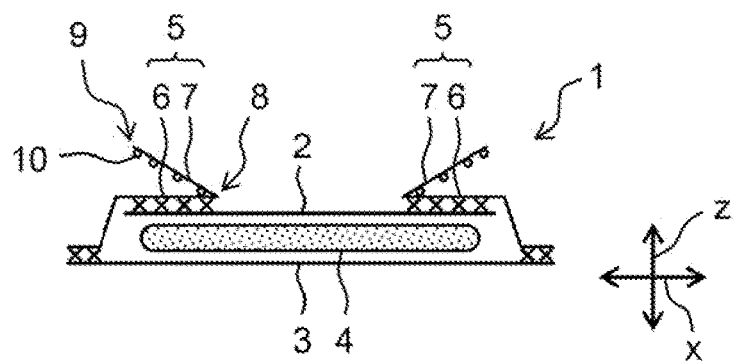
FIG. 2 shows a cross-sectional view along a line II-II of the absorbent article shown in FIG. 1.
Figure 3:
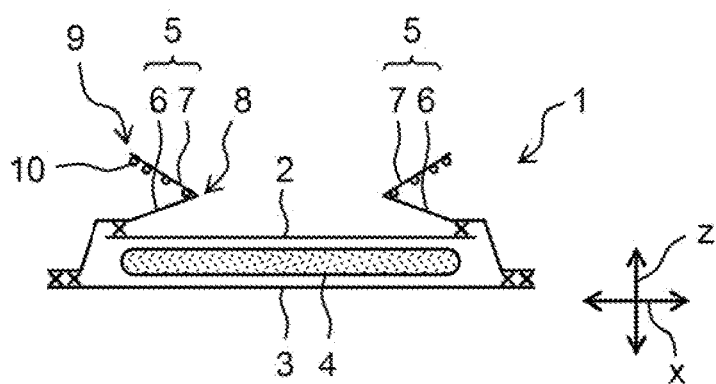
FIG. 3 shows a cross-sectional view along a line III-III of the absorbent article shown in FIG. 1.
Figure 4:
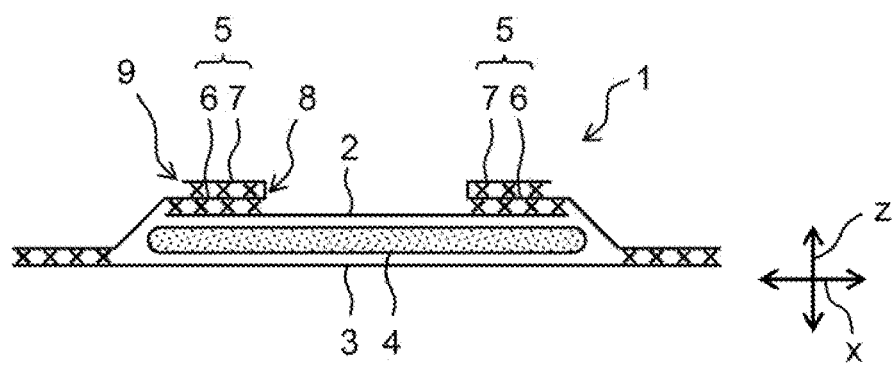
FIG. 4 shows a cross-sectional view along a line IV-IV of the absorbent article shown in FIG. 1.

FIGS. 1 to 4 show an example of the absorbent article of the present invention, that is applied to an open-type (tape-type) disposable diaper. FIG. 1 shows a plan view of an open-type disposable diaper seen from a skin-facing side, and FIGS. 2, 3 and 4 show cross-sectional views take along line II-II, line III-III and line IV-IV of the disposable diaper shown in FIG. 1, respectively. In the drawings, an arrow x represents the width direction and an arrow y represents the front-rear direction, and a direction orthogonal to the arrows x and y represents a thickness direction.

An absorbent article (an open-type disposable diaper) 1 comprises a top sheet 2, a back sheet 3 and an absorbent core 4 provided therebetween. The top sheet 2 is provided on a skin-facing side of the absorbent article 1 and allows urine and the like excreted from a wearer to permeate through. The urine and the like which has passed through the top sheet 2 is accommodated in the absorbent core 4. The back sheet 3 is provided on an exterior side of the absorbent article 1 and prevents the excrement from permeating outside. In the absorbent article 1, the absorbent core 4 is formed in an hourglass shape.

Flap sheets 5 are provided on both sides of the top sheet 2 in the width direction x. The flap sheet 5 has a center region C, end regions E and intermediate regions M positioned therebetween in the front-rear direction y (FIG. 1). The end region E includes a front end region E1 and a rear end region E2, formed in a front side and a rear side of the absorbent article 1, respectively, and the intermediate region M includes a front intermediate region M1 and a rear intermediate region M2, formed in a front side and a rear side of the absorbent article 1, respectively.

The flap sheet 5 has a base part 6 facing to the top sheet 2 and a rising part 7 extending from the base part 6 and formed by folding at an inner edge 8 of the base part 6 in the width direction x, as shown in FIGS. 2 to 4. An outer edge 9 of the rising part 7 is made to be a free end.

FIG. 2 shows a cross-sectional view of the absorbent article 1 at the center region C, FIG. 3 shows a cross-sectional view of the absorbent article 1 at the intermediate region M, FIG. 4 shows a cross-sectional view of the absorbent article 1 at the end region E; and the center region C and the end region E of the base part 6 are joined to the top sheet 2 at an inner position, in the width direction x, of that the intermediate region M of the base pan 6 is joined to the top sheet 2, and the rising part 7 is joined to the base part 6 at the end region E. In FIG. 1, a place where the flap sheet 5 is joined to the top sheet 2 or the back sheet 3 (that is, where a joining area is formed) is expressed by cross-hatching. In FIGS. 2 to 4, a place where the base part 6 is joined to the top sheet 2 or the back sheet 3 and a place where the rising part 7 is joined to the base part 6 are expressed by crosses (X). As the flap sheet 5 is formed in this manner in the absorbent article 1, the rising part 7 easily stands outward in the width direction x, whereby urine and the like excreted from a wearer is received properly. Further, even when the wearer sits, the flap sheet 5 easily stands outward in the width direction x stably at the center region C. Meanwhile, the intermediate region M of the flap sheet 5 is less likely to be pressed when the wearer sits, and therefore, a leakproof wall which is formed by the flap sheet 5 can be formed high, whereby lateral leakage of urine and the like is easily prevented.

In FIGS. 2 to 4, the base part 6 is joined to the top sheet 2 at an inner end of the joining area (an inner end in the width direction x) in the center region C, the intermediate region M and the end region E; however, in the case where the back sheet 3 extends outward beyond the top sheet 2 in the width direction x or the back sheet 3 is folded along an edge, with respect to the width direction x, of the absorbent core 4 onto an upper surface of the top sheet 2, the base part 6 may be joined to the back sheet 3 at the inner end of the joining area in the intermediate region M or further in the center region C and the end region E.

In the rising part 7, a plurality of flap elastic members 10 extending in the front-rear direction y are disposed so as to be arranged in the width direction x. Meanwhile, the base part 6 is not provided with an elastic member. When the rising part 7 is provided with the flap elastic members 10, the rising part 7 easily stands outward in the width direction x in a planar state, thereby contacting wearer's skin so as to encompass buttocks of a wearer. The flap elastic member 10 is preferably disposed so as to extend from the center region C to the front intermediate region M1 and the rear intermediate region M2, as shown in FIG. 1.

In the absorbent article 1, fastener members 11 are attached to left and right ends of a rear part (a rear part in the front-rear direction y) of the absorbent article 1, and a fastener-receiving part 12, which the fastener member 11 is joined to in wearing, is provided on the back sheet 2 in a front part (a front part in the front-rear direction y) of the absorbent article 1. For example, the fastener member 11 is provided with a hook member of a hook-and-loop fastener and the fastener-receiving part 12 is composed of a loop member of a hook-and-loop fastener. The absorbent article 1 can be worn by applying to a wearer's crotch and attaching the fastener member 11 to the fastener-receiving part 12.

A waist elastic member 13 is provided at an end part, with respect to the front-rear direction y, of the absorbent article 1. The waist elastic member 13 is disposed, for example, between the top sheet 2 or the flap sheet 5 and the back sheet 3. A waist-gather around a wearer's waist is formed by the waist elastic member 13, thereby preventing excrement such as urine and the like from leaking from a back side or an abdomen side.

A leg elastic member 14 is provided on both sides, in the width direction x, of the absorbent article 1 at an outer position, in the width direction x, of the absorbent core 4. The leg elastic member 14 is disposed, for example, between the flap sheet 5 and the back sheet 3. Leg-gathers around wearer's legs are formed by the leg elastic member 14, thereby preventing excrement such as urine and the like from leaking from a crotch. In the FIGS. 2 and 3, the leg elastic member 14 is omitted.

Figure 5:
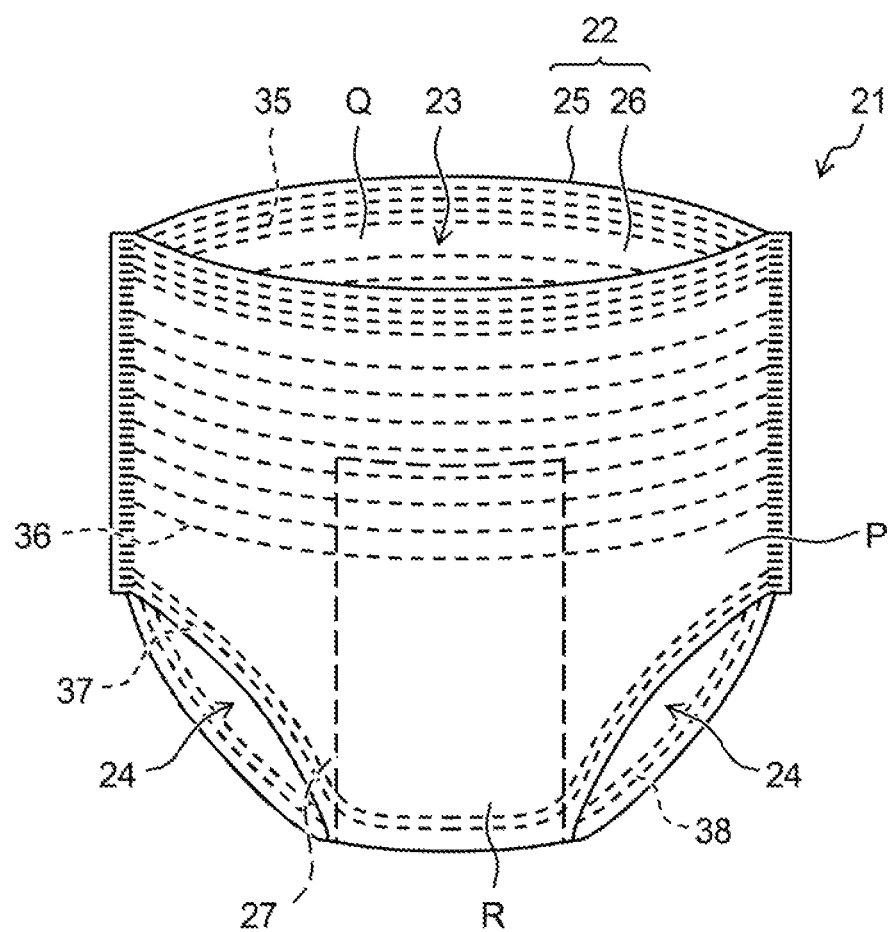
FIG. 5 shows a perspective view of a pants-type disposable diaper as an absorbent article.
Figure 6:
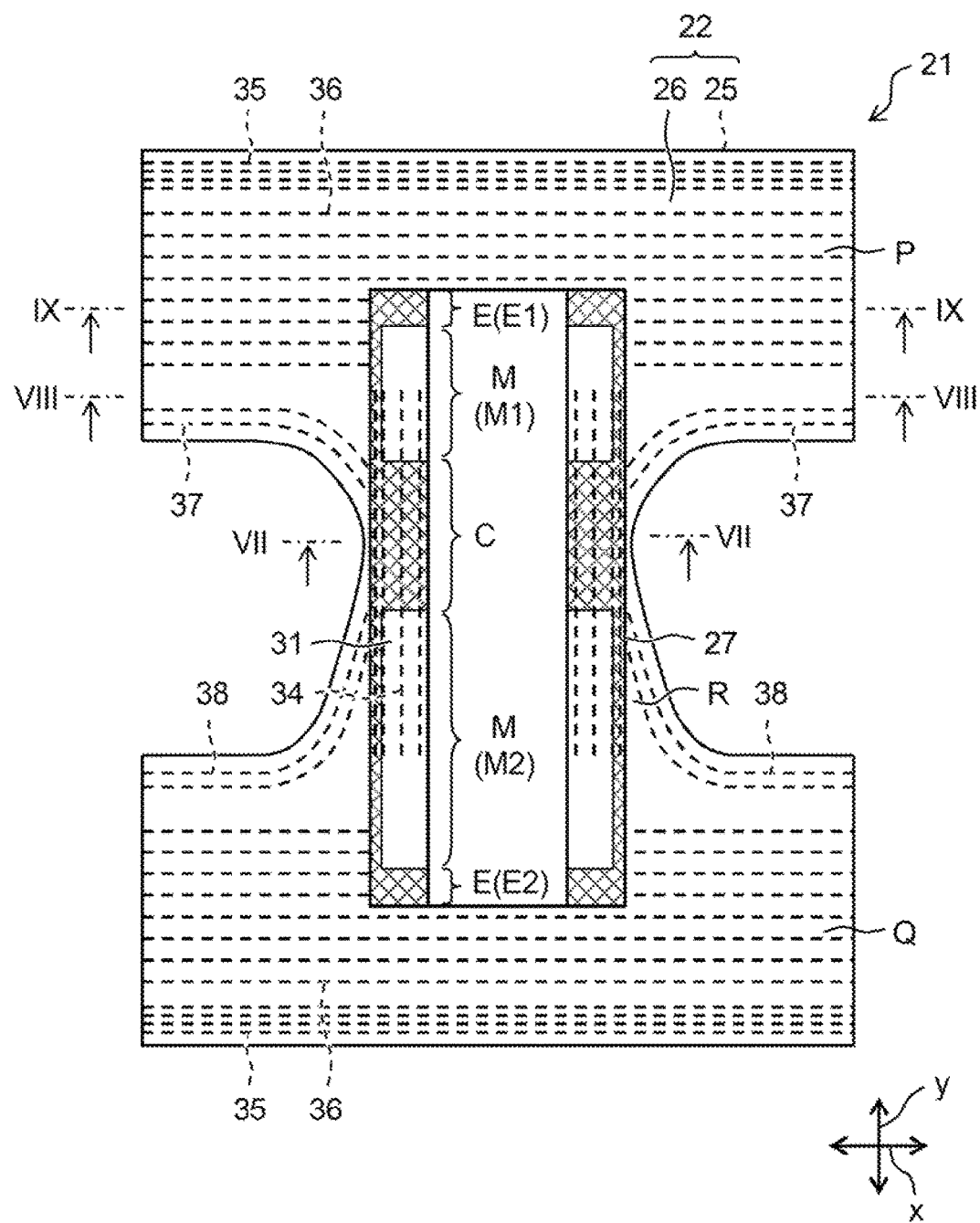
FIG. 6 shows a plan view of a skin-facing side of the absorbent article (the pants-type disposable diaper) shown in FIG. 5 in a developed state in which a front part and a rear part are disjoined.
Figure 7:
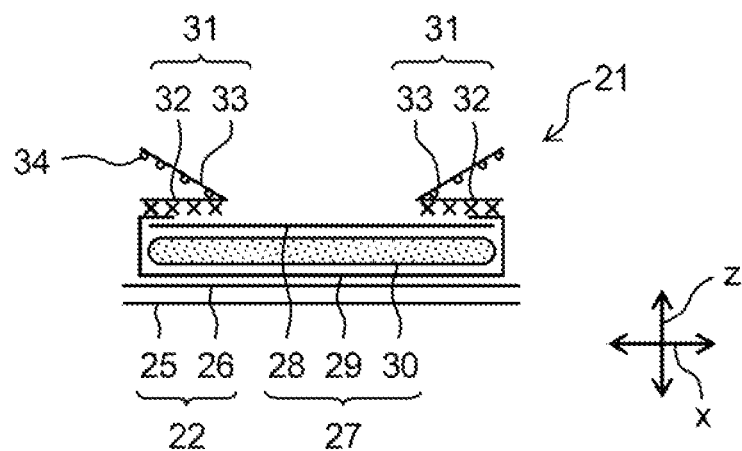
FIG. 7 shows a cross-sectional view along a line VII-VII of the absorbent article shown in FIG. 6.
Figure 8:
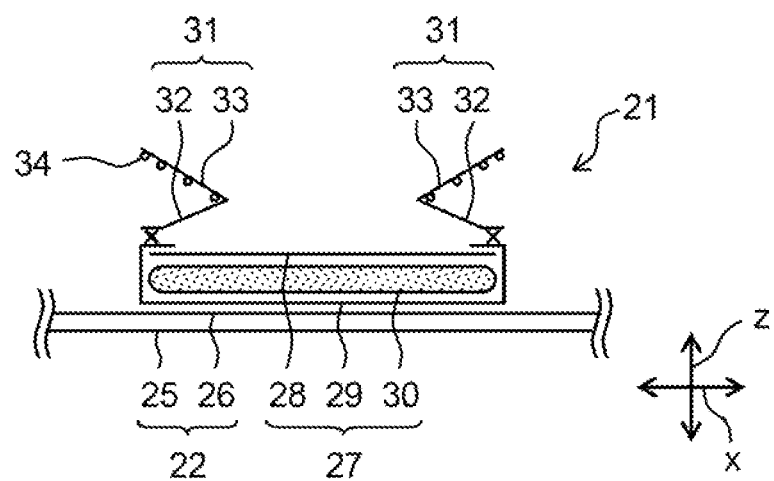
FIG. 8 shows a cross-sectional view along a line VIII-VIII of the absorbent article shown in FIG. 6.
Figure 9:
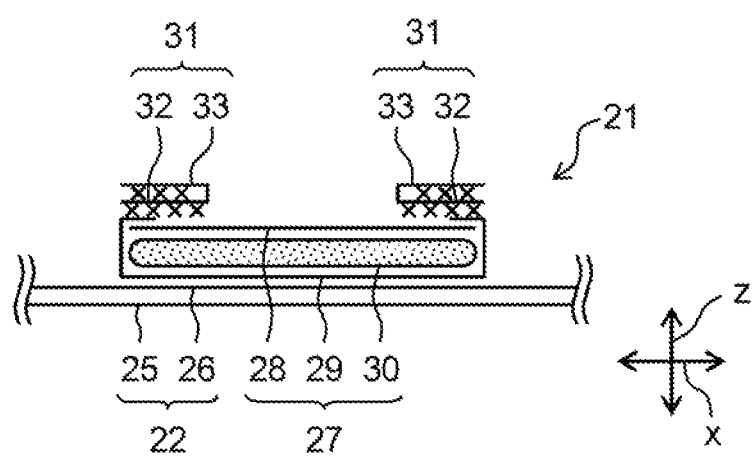
FIG. 9 shows a cross-sectional view along a line IX-IX of the absorbent article shown in FIG. 6.

Next, another example of the absorbent article of the present invention is explained. FIGS. 5 to 9 show an example of the absorbent article of the present invention, that is applied to a pants-type disposable diaper. FIG. 5 shows a perspective view of a pants-type disposable diaper; FIG. 6 shows a plan view of the pants-type disposable diaper shown in FIG. 5 in a developed state in which a front part and a rear part are disjoined, and seen from a skin-facing side; and FIGS. 7, 8 and 9 show cross-sectional views take along line VII-VII, line VIII-VIII and line IX-IX of the disposable diaper shown in FIG. 6, respectively. In the following, explanations overlapping the above description are omitted.

An absorbent article (a pants-type disposable diaper) 21 comprises: an exterior member 22 having a waist opening 23 and a pair of leg openings 24 and formed in a pants shaped; and an absorbent body 27 provided on a skin-facing side of the exterior member 22. The exterior member 22 has a front part P, a rear part Q and a crotch part R positioned therebetween, and formed into a pants shape by joining the front part P and the rear part Q. The exterior member 22 comprises an outer sheet 25 and an inner sheet 26 laminated on a skin-facing side of the outer sheet 25.

The absorbent body 27 is disposed on the skin-facing side of the exterior member 22 at least at the crotch part R, and comprises a top sheet 28, a back sheet 29 and an absorbent core 30 provided therebetween (FIGS. 7 to 9). In the absorbent article 21, the absorbent body 27 and the absorbent core 30 are formed in a substantially rectangular shape. The back sheet 29 is folded along an edge of the absorbent core 30 in the width direction x and overlapped on an upper surface of the top sheet 28 to be joined.

The absorbent body 27 is provided with flap sheets 31 on both sides of the top sheet 28 in the width direction x. FIG. 7 shows a cross-sectional view of the absorbent article 21 at the center region C, FIG. 8 shows a cross-sectional view of the absorbent article 21 at the intermediate region M, FIG. 9 shows a cross-sectional view of the absorbent article 21 at the end region E; and the flap sheet 31 has a base part 32 facing to the top sheet 28 and a rising part 33 extending from the base part 32 and formed by folding at an inner edge of the base part 32 in the width direction x. The rising part 33 is provided with a flap elastic member 34.

In the absorbent article 21, the base part 32 is joined to the top sheet 28 at an inner end of the joining area (an inner end in the width direction x) in the center region C and the end region E, while in the intermediate region M, the base part 32 is joined to the back sheet 29 at the inner end of the joining area. Thus, in the absorbent article 21, the center region C and the end region E of the base part 32 are joined to the top sheet 28 and/or the back sheet 29 at an inner position, in the width direction, of that the intermediate region M of the base part 32 is joined to the top sheet 28 and/or the back sheet 29; and the rising pan 33 is joined to the base part 32 at the end region E. In FIG. 6, a place where the flap sheet 31 is joined to the top sheet 28 or the back sheet 29 (that is, where a joining area is formed) is expressed by cross-hatching. In FIGS. 7 to 9, a place where the base part 32 is joined to the top sheet 28 or the back sheet 29 and a place where the rising part 33 is joined to the base part 32 are expressed by crosses (X). In the absorbent article 21, the same effects as in the absorbent article shown in FIGS. 1 to 4 are exerted, as to the flap sheet 31 and the flap elastic member 34.

A plurality of waist elastic members 35 are disposed along an edge of the waist opening 23 at an end part, with respect to the front-rear direction y, of the exterior member 22. A waist-gather around a wearer's waist is formed by the waist elastic member 35, thereby preventing excrement such as urine and the like from leaking from a back side or an abdomen side.

A plurality of body elastic members 36 extending in the width direction x are disposed at the front part P and the rear part Q of the exterior member 22. The body elastic members 36 are disposed between the waist elastic member 35 and the leg openings 24, and arranged at wider intervals than the waist elastic member 35. The body elastic member 36 functions to improve fittability around a wearer's belly.

Leg elastic members 37, 38 are disposed in the exterior member 22 along an edge of the leg opening 24. The leg elastic member consists of a front leg elastic member 37 disposed along a front side of the edge of the leg opening 24 and a rear leg elastic member 38 disposed along a rear side of the edge of the leg opening 24. By the front leg elastic member 37 and the rear leg elastic member 38, the leg elastic member is provided along almost the entire circumference of the edge of the leg opening 24. Leg-gathers around wearer's legs are formed by the leg elastic members 37, 38, thereby preventing excrement such as urine and the like from leaking from a crotch.

The waist elastic member 35, the body elastic member 36 and the leg elastic members 37, 38 are disposed, for example, between the outer sheet 25 and the inner sheet 26, and adhered to the outer sheet 25 and/or the inner sheet 26 in their stretched states. The outer sheet 25 may be folded back at the edge of the waist opening 24 of the exterior member 22 toward the inner sheet 26, and the waist elastic member 35 may be interposed between the folded and unfolded parts of the outer sheet 25 and adhered to the outer sheet 25.

This application claims priority to Japanese Patent Application No. 2013-55621, filed on Mar. 18, 2013, the entire contents of which are incorporated by reference herein.

REFERENCE SIGNS LIST 1, 21: an absorbent article
2, 28: a top sheet
3, 29: a back sheet
4, 30: an absorbent core
5, 31: a flap sheet
6, 32: a base part
7, 33: a rising part
10, 34: a flap elastic member
22: an exterior member
27: an absorbent body
C: a center region
M, M1, M2: an intermediate region
E, E1, E2: an end region

The invention claimed is:

1. An absorbent article comprising a top sheet, a back sheet and an absorbent core provided therebetween, and having a front-rear direction and a width direction, wherein:
flap sheets having a center region, end regions and intermediate regions positioned between the center region and the end regions, wherein the flap sheets are provided on both sides of the top sheet in the width direction;
the flap sheet has a base part facing the top sheet and a rising part extending from the base part, the rising part being formed by folding the flap sheet at an inner edge of the base part in the width direction;
the base part is joined to the top sheet and/or the back sheet over a joining area;
inner ends of the joining areas of the center region and the end regions of each of the flap sheets are located closer in the width direction toward a center of the absorbent core than inner ends of the joining areas of the intermediate regions; and
the rising part is joined to the base part at the end regions.

2. The absorbent article according to claim 1, wherein the rising part is provided with a flap elastic member extending in the front-rear direction and the base part is not provided with an elastic member.

3. The absorbent article according to claim 2, wherein a plurality of the flap elastic members are disposed so as to be arranged in the width direction.

4. The absorbent article according to claim 3, wherein
at least one elastic member is disposed in an area within 5 mm from an outer edge of the rising part in the width direction, as the flap elastic member, and
at least one elastic member is disposed in an area within 5 mm from an inner edge of the rising part in the width direction, as the flap elastic member.

5. The absorbent article according to claim 3, wherein the flap elastic members are disposed in the rising part such that contraction force in an outer side, with respect to the width direction, of the rising part is larger than that in an inner side, with respect to the width direction, of the rising part.

6. The absorbent article according to claim 2, wherein the flap elastic member is attached to the rising part with an adhesive and disposed so as to extend from the center region to the front and rear intermediate regions, wherein an amount of the adhesive applied to a front end part of the flap elastic member is larger than that applied to a rear end part of the flap elastic member.

7. The absorbent article according to claim 1, wherein the center region and the end region of the base part are joined to the top sheet and/or the back sheet at a 10 mm or more inner position, in the width direction, of that the intermediate region of the base part is joined to the top sheet and/or the back sheet.

8. The absorbent article according to claim 1, wherein the center region of the base part is joined to the top sheet at an area within 10 mm from the inner edge of the base part in the width direction.

9. The absorbent article according to claim 1, wherein the joining area joining the base part to the top sheet and/or the back sheet extends continuously toward the center of the absorbent core.

10. The absorbent article according to claim 1, wherein the joining area joining the base part to the top sheet and/or the back sheet extends intermittently toward the center of the absorbent core.

\* \* \* \* \*